United States Patent [19]

Coveney

[11] Patent Number: 4,801,454
[45] Date of Patent: Jan. 31, 1989

[54] PROCESSES FOR MAKING COLORED PHARMACEUTICAL COMPOSITIONS

[75] Inventor: Leila D. Coveney, Cincinnati, Ohio

[73] Assignee: The Proctor & Gamble Company, Cincinnati, Ohio

[21] Appl. No.: 887,671

[22] Filed: Jul. 17, 1986

[51] Int. Cl.$^4$ .................... A61K 33/24; A61K 31/29
[52] U.S. Cl. ..................................... 424/131; 514/503
[58] Field of Search ................. 424/131; 514/159, 503

[56] References Cited

FOREIGN PATENT DOCUMENTS 52-26909 2/1977 Japan .

OTHER PUBLICATIONS

Handbook of Non-Prescription Drugs 35 (5th Edition, 1977).

*Primary Examiner*—Frederick E. Waddell
*Attorney, Agent, or Firm*—David L. Suter; Kim William Zerby; Richard C. Witte

[57] ABSTRACT

Processes for making colored pharmaceutical compositions, by the steps of:

(a) preparing an aqueous mixture having a pH of at least about 5, containing a suspension agent, and a pharmaceutically-acceptable bismuth salt at a level of from about 0.5% to about 3%, by weight of final composition;

(b) adding a quantity of FD&C Red 3 dye to the mixture;

(c) mixing the mixture for at least about 30 seconds; and (d) adjusting the pH of the mixture to a pH in the range of from about 3.4 to about 4.

Preferably, the bismuth salt is bismuth subsalicylate. Preferred suspension agents include mixtures of magnesium aluminum silicate and methyl cellulose and of magnesium aluminum silicate and xanthan gum.

9 Claims, No Drawings

PROCESSES FOR MAKING COLORED PHARMACEUTICAL COMPOSITIONS

BACKGROUND OF THE INVENTION

This invention relates to processes for making colored pharmaceutical compositions useful in humans and other animals. In particular, it relates to such compositions, useful for the treatment of gastrointestinal disorders, containing an aqueous suspension of a bismuth-containing active material onto which a dye has been adsorbed.

Liquid suspensions can be generally defined as two-phase systems, wherein a finely divided solid is dispersed in a liquid medium. Many such formulations are described in the pharmaceutical literature, incorporating a variety of materials as suspending agents. See, for example, M. Pernarowski, "Solutions, Emulsions, and Suspensions", *Remington's Pharmaceutical Sciences*, Chapter 83 (A. Osol, et al., ed., 15th edition 1975), and *The Theory and Practice of Industrial Pharmacy* (L. Lachman, et al., ed., 2d edition 1976). One such product is sold by The Procter & Gamble Company under the trademark "Pepto-Bismol", for the treatment of nausea, heartburn, diarrhea and other gastrointestinal disorders. This product comprises an aqueous suspension of bismuth subsalicylate (at a level of about 1.75%, by weight) with methylcellulose and magnesium aluminum silicate. The formulation exhibits a high degree of consumer acceptability, with a color and viscosity which is particularly preferred. Indeed, the pink color of Pepto-Bismol® is commercially recognized and distinctly associated with the product and its generic copies. This color can be defined according to the L-a-b reflectance colorimetry scale, as approximately (L,a,b)=(56, 48, −1.8), as measured on a Colorgard System 05 Colorimeter, Model 2000. The product employs a mixture of dyes to obtain this pink color: FD & C Red No. 3 and FD & C Red No. 40.

Pepto-Bismol is manufactured in a process which generally comprises the steps of first making an aqueous solution of the suspension agents (magnesium aluminum silicate and methylcellulose), followed by addition of FD & C Red 3 dye. The pH of this mixture is typically about 9.6. The bismuth subsalicylate is then added, as an aqueous slurry, lowering the product pH to approximately 6.5. The product is mixed, and then salicylic acid, sodium salicylate, FD & C Red 40 dye, sodium saccharin and a flavorant are added. The product pH is then about 3.5. Finally, the product is homogenized and packaged.

In the manufacture of any colored composition, it is important to maintain uniformity and reproducibility of color. Such uniformity is particularly important in the manufacture of products such as Pepto-Bismol, which are commercially-associated with a particular color. Further, the color of the product should remain stable, and not significantly change under typical conditions of storage. Such stability includes resistance to color fading from exposure to ultra-violet (fluorescent) light. The processes used to manufacture such products should also be easily implemented on a commercial production scale, and should be appropriate for production of pharmaceutically-acceptable products. It has been found that in the manufacture of Pepto-Bismol certain processing steps must be employed in order to obtain a preferred, colored product. In particular, it has been discovered that methods for manufacturing such bismuth-containing compositions, utilizing a particular order of processing steps, yield products with more uniform, reproducible and stable color than processes known in the art. Such processes of this invention also yield other advantages in maintaining the physical and chemical stability of the composition and its components, and in being readily implemented on a commercial production scale.

SUMMARY OF THE INVENTION

The present invention provides processes, for making colored pharmaceutical compositions, comprising the steps of:

(a) preparing an aqueous mixture having a pH of at least about 5, containing a suspension agent, and a pharmaceutically-acceptable bismuth salt at a level of from about 0.5% to about 3%, by weight of final composition;

(b) adding a quantity of FD & C Red 3 dye to said mixture;

(c) mixing said mixture for at least about 30 seconds; and (d) adjusting the pH of said mixture to a pH in the range of from about 3.4 to about 4.

A preferred bismuth salt is bismuth subsalicylate. Preferably, the compositions made by the processes of this invention contain other colorants, as well as flavorants. As described above, these processes and the products made by these processes afford advantages in manufacturing and product acceptability over methods known in the art. Such advantages include, for example, stability, uniformity and reproducibility of product color, as well as stability of the overall product formulation.

DESCRIPTION OF THE INVENTION

Components and Compositions

The compositions made by the processes of the present invention are aqueous suspensions of a water-insoluble, pharmaceutically-acceptable bismuth salt onto which is adsorbed a red dye. These processes and compositions, accordingly, employ three essential components, in addition to water: a pharmaceutically-acceptable bismuth salt, a suspension agent, and a red dye material. In addition, the compositions of the present invention may contain optional pharmaceutically-acceptable components which may modify their physical characteristics and/or their therapeutic effects.

All components of the present compositions must, of course, be pharmaceutically-acceptable. As used herein, a "pharmaceutically-acceptable" component is one which is suitable for use with humans and/or other animals without undue adverse side effects (such as toxicity, irritation and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation or allergic response) commensurate with a reasonable benefit/risk ratio when used in the manner of this invention. The specific "safe and effective amount" will, obviously, vary with such factors as the particular condition that is being treated, the severity of the condition, the duration of the treatment, the physical condition of the patient, the nature of concurrent therapy (if any), and the specific formulation and optional components employed.

The compositions made by the processes of this invention are aqueous suspensions comprising:
(a) from about 0.5% to about 3% of a pharmaceutically-acceptable bismuth salt;
(b) a suspension agent in an amount sufficient to suspend said bismuth salt in said composition; and
(c) from about 0.005% to about 0.3% of FD & C Red 3 dye;

wherein the pH of said composition is from about 3.4 to about 4.0. Preferably the composition contains a second dye selected from the group consisting of FD & C Red 40; D & C Red 22, and mixtures thereof. These compositions typically contain water at levels of from about 93% to about 98%. (Unless otherwise specified, all percentages herein are by weight of final composition.)

The compositions made by the present processes contain a pharmaceutically-acceptable bismuth salt at a level of from about 0.5% to about 3%, preferably, from about 1% to about 2.5%, more preferably from about 1.5% to about 2%. These bismuth salts are essentially water-insoluble, i.e., less than 1% (by weight of salt) soluble in water. Such salts include, for example, bismuth aluminate, bismuth citrate, bismuth subcitrate, bismuth nitrate, bismuth subcarbonate, bismuth subgalate, bismuth tartrate, and bismuth subsalicylate, and mixtures thereof. A particularly preferred bismuth salt useful herein is bismuth subsalicylate (2-hydroxybenzoato-O-oxobismuth; basic bismuth $III^{+2}$-hydroxybenzoate).

The present invention employs a suspension system comprising one or more compounds (herein "suspension agents") which maintain the bismuth salt in an essentially uniform aqueous suspension at typical conditions of storage and use. Such suspension systems, suspension agents, and methods of their use include those well known in the art. See, for example, M. Pernarowski, "Solutions, Emulsions and Suspensions" *Remington's Pharmaceutical Sciences* (A. Osol, editor, 5th Edition, 1975), incorporated by reference herein. One preferred suspension system employs a mixture of methyl cellulose and magnesium aluminum silicate. In such a system, methyl cellulose may be used at levels of from about 0.5% to about 1.5%, and magnesium aluminum silicate may be used at levels of from about 0.5% to about 1.5%. Methylcellulose, or cellulose methyl ether, is commercially available from a variety of sources as a chemically treated plant cellulose derivative. Among such methyl cellulose materials useful herein is Methocel, sold by Dow Chemical Company. Magnesium aluminum silicate (or aluminum magnesium silicate) is of the formula $Al_2MgO_8Si_2$, occurring naturally in such smectite minerals as colerainite, saponite, and sapphirine. Refined magnesium aluminum silicates useful herein are readily available, such as Veegum, manufactured by R. T. Vanderbilt Company, Inc.

Another particularly preferred suspension system useful in the present invention is a mixture of xanthan gum and magnesium aluminum silicate. In such a system, xanthan gum is used at a level of from about 0.5% to about 0.85%, preferably from about 0.55% to about 0.75%. Magnesium aluminum silicate is used at a level of from about 0.3% to about 1.3%, preferably from about 0.5% to about 1.0%. Xanthan gum is a high molecular weight polysaccharide produced through pure culture fermentation of carbohydrates by the microorganism *Xanthomonas campestris*. Xanthan gum is further described in L. Cottrell, et al., *Handbook of Water soluble Gums and resins*, Chapter 24 (R. Davidson ed., 1980), incorporated by reference herein. Xanthan gum is available from a variety of commercial sources, including Rhodigel (sold by Rhone Poulenc Industries) and Keltrol (sold by Kelco Division of Merck & Company, Inc.)

The present compositions contain FD & C Red 3 dye at a level of from about 0.005% to about 0.03%, preferably from about 0.01% to about 0.02%. "FD & C Red 3" is the designation, ascribed by the Food and Drug Administration, to erythrosine, or the disodium salt of 9-(o-carboxyphenyl)-6-hydroxy-2,4,5,7,-tetraiodo-3-isoxanthone.

The compositions of the present invention may also contain optional components which modify the physical characteristics and/or therapeutic effects of the composition. Such optional components must not, however, substantially affect, in an adverse manner, the therapeutic activity of the bismuth salt used in the composition. The optional components useful herein must not also substantially affect adsorption of the red dyes onto the bismuth salt. Preferred optional components useful herein include preservatives, optional colorants, sweeteners, and flavorants, typically at levels of from about 0.01% to about 0.2%.

Particularly preferred optional components are additional colorants used to impart particular shades of pink to the compositions. These optional colorants may be added during any step of the processes of this invention. The particular color of the products of this invention may be measured by a colorimeter, yielding reflectance measurements of L, a, and b reflectance variables. The "L" variable refers to the intensity or lightness of the color. The "a" variable refers to the red/green coloration, wherein a positive "a" value is red, and a negative "a" value is green. The "b" variable refers to the yellow/blue coloration, wherein a positive "b" value is yellow, and a negative "b" value is blue. As measured on a Colorgard System 05 Colorimeter, Model 2000 (sold by Pacific Scientific Company), one preferred product of this invention has a color reflectance of about $(L,a,b) = (56,48,-1.8)$. Accordingly it is preferred to employ optional colorants in the products, selected from FD & C Red 40 (Allura Red AC), D & C Red 22 (Eosin YS, Eosine G), and mixtures thereof. Particular mixtures of these optional dyes with the FD & C Red 3 dye may be used to obtain the desired preferred product color. For example, a preferred mixture of FD & C Red 3 and Red 40 dyes is in the weight ratio of Red 3:Red 40 of from about 1:0.15 to about 1:1. It should be noted that the color of the product will also vary with the relative amounts of dye and bismuth salt employed.

METHODS

The processes of this inventin comprise the steps of:
(a) preparing an aqueous mixture having a pH of at least about 5, containing suspension agent, and a pharmaceutically-acceptable bismuth salt at a level of from about 0.5% to about 3%, by weight of final composition;
(b) adding a quantity of FD & C Red 3 dye to said mixture;
(c) mixing said mixture for at least about 30 seconds; and
(d) adjusting the pH of said mixture to a pH in the range of from about 3.4 to about 4.

These steps may be conducted in a batch production process, or as discrete steps in a continuous production process. Optional components, as described above, may also be incorporated into the compositions made by the present processes.

The mixture preparing step (a) may be performed by any suitable means of obtaining a suspension of the bismuth salt in water. In one process of this invention, the suspension agent is dissolved in purified water, and thoroughly mixed. The bismuth salt is preferably added as a slurry, i.e., a concentrated mixture of the bismuth salt and water. This slurry is added to the suspension agent aqueous mixture, and mixed to form an aqueous suspension of the bismuth salt.

In the present processes, the pH of the product mixture during the dye adding step (b) of the process described above, is preferably from about 5 to about 9, more preferably from about 5.5 to about 8.0. For compositions having a suspension agent consisting of a mixture of magnesium aluminum silicate and methyl cellulose, or of magnesium aluminum silicate and xanthan gum, the pH of the product mixture at the completion of the mixture preparing step (a) is from about 5 to about 7. However, for product mixtures having a pH less than about 5, the present processes preferably include a step, immediately prior to the dye adding step (b), of adjusting the pH of the mixture to a pH of at least about 5, preferably from about 5.5 to about 8. This pH adjusting step is effected by raising the pH through addition of a pharmaceutically-acceptable base. Such base materials useful herein include, for example, sodium hydroxide, potassium hydroxide, and mixtures thereof.

The mixing step (c) may consist of any method of ensuring complete contact between the dyes and the bismuth salt, and is performed for at least about 30 seconds, preferably at least about 5 minutes, more preferably from about 10 to about 20 minutes. After the mixing step (c), the pH of the product mixture is adjusted, in step (d), to a pH of from about 3.4 to about 4.0, preferably from about 3.4 to about 3.6. This adjustment is effected by addition of a pharmaceutically-acceptable acid. When bismuth subsalicylate is employed as the bismuth salt, a preferred acid for use in the pH adjustment step (d) is salicylic acid. Preferably, as part of the pH adjustment step (d), the product is mixed to ensure its uniformity. This mixing may include homogenization, using any of a variety of commercially-acceptable homogenizers. As will be appreciated by those skilled in the art, the conditions under which the compositions are mixed and homogenized may have an effect on the product viscosity. The compositions of this invention preferably have a viscosity of from about 100 to about 400 centipoises (cps), more preferably from about 110 to about 250 cps as measured on a Hoeppler Viscosimeter (manufactured by Cannon Instrument Company). As measured with a Wells Brookfield Viscometer, (Model RVTDCP with a CP-41 cone, manufactured by Brookfield Engineering Laboratories, Inc.), at about 10 cone rpm, the viscosity of the present compositions is preferably from about 100 to about 350 cps, more preferably from about 200 to about 250 cps.

The methods by which the present compositions are used will depend upon such factors as the particular bismuth salt incorporated, the particular condition being treated, the physical condition of the patient, and the nature of concurrent therapy (if any). These compositions are typically administered orally, for the treatment of gastrointestinal disorders, so that from about 50 to about 5,000 milligrams, preferably from about 500 to about 1,500 milligrams, of bismuth is administered per day (measured by weight of elemental bismuth).

The following non-limiting examples illustrate the compositions, processes and uses of the present invention.

EXAMPLE 1

A composition, according to the present invention, is made comprising:

| Component | % (by weight) |
|---|---|
| bismuth subsalicylate | 1.7500 |
| magnesium aluminum silicate | 0.9850 |
| methyl cellulose | 1.0790 |
| FD&C Red 3 dye | 0.0104 |
| FD&C Red 40 dye | 0.0054 |
| salicylic acid | 0.0706 |
| sodium salicylate | 0.0598 |
| flavorant | 0.0881 |
| sodium saccharin | 0.0608 |
| water | 95.8909 |

A batch composition, comprised as above, was made by first mixing the veegum in a quantity of water, followed by addition of the methyl cellulose. The suspension system was then mixed for approximately 30 minutes. The pH of the aqueous mixture was then approximately 9.7. The bismuth subsalicylate was added, as a slurry of approximately 9% salt in water, and mixed for approximately 25 minutes. The pH of the aqueous mixture was then approximately 6. The FD & C Red 3 was then added, and the product mixed for approximately 10 minutes. The FD & C Red 40 dye was added, and mixed for approximately 12 minutes. The salicylic acid, sodium salicylate, flavorant and sodium saccharin were then added, and mixed for approximately 9 minutes. The final batch product pH was approximately 3.5. The batch product was then filled into individual bottles.

The composition of the above Example, when administered to a human having diarrhea, is effective to lessen the severity of symptoms.

EXAMPLE 11

A composition, according to the present invention, is made comprising:

| Component | % (by weight) |
|---|---|
| bismuth subsalicylate | 1.7500 |
| magnesium aluminum silicate | 1.0000 |
| xanthan gum | 0.7000 |
| FD&C Red 3 | 0.0104 |
| FD&C Red 40 | 0.0054 |
| salicylic acid | 0.0706 |
| sodium salicylate | 0.0598 |
| flavorant | 0.0881 |
| sodium saccharin | 0.0608 |
| water | 96.2549 |

A composition comprised as above is made by thoroughly mixing the magnesium aluminum silicate and xanthan gum in water. The bismuth subsalicylate is then added, as part of an aqueous slurry, and the product mixed. The pH of the composition is measured and found to be greater than approximately 5.5. The FD & C Red and FD & C Red 40 dyes are then added, and mixed. The remaining components are then added, and the product mixed and homogenized.

In the above Example, bismuth subgalate, bismuth subcarbonate, bismuth citrate, bismuth nitrate, and bismuth aluminate are substituted, respectively, for bismuth subsalicylate, with substantially-similar results.

What is claimed is:

1. A process for making a color-stable pharmaceutical composition, comprising the steps of:
   (a) preparing an aqueous mixture having a pH of at least about 5, containing a suspension agent, and a pharmaceutically-acceptable bismuth salt at a level of from about 0.5% to about 3%, by weight of final composition;
   (b) adding a quantity of FD & C Red 3 dye to said mixture;
   (c) mixing said mixture for at least about 30 seconds; and
   (d) adjusting the pH of said mixture to a pH in the range of from about 3.4 to about 4.

2. A process for making a color-stable pharmaceutical composition, according to claim 1, wherein said bismuth salt is selected from the group consisting of bismuth aluminate, bismuth subcarbonate, bismuth citrate, bismuth subcitrate, bismuth nitrate, bismuth subgalate, bismuth tartrate, bismuth subsalicylate and mixtures thereof.

3. A process for making a color-stable pharmaceutical composition, according to claim 2, wherein said bismuth salt is bismuth subsalicylate.

4. A process for making a color-stable pharmaceutical composition, according to claim 3, wherein said pH adjusting step (d) is performed by adding salicylic acid to said mixture.

5. A process for making a color-stable pharmaceutical composition, according to claim 3, wherein said bismuth salt is present at a level of from about 1.5% to about 2%.

6. A process for making a color-stable pharmaceutical composition, according to claim 5, wherein said composition additionally comprises FD & C Red 40 dye.

7. A process for making a color-stable pharmaceutical composition, according to claim 2, wherein said aqueous mixture of step (a) has a pH in the range of from about 5.5 to about 8.

8. A process for making a color-stable pharmaceutical composition, according to claim 7, wherein said suspension agent comprises a mixture of magnesium aluminum silicate and methyl cellulose.

9. A process for making a color-stable pharmaceutical composition, according to claim 7, wherein said suspension agent comprises a mixture of magnesium aluminum silicate and xanthan gum

* * * * *